United States Patent
Narducy et al.

[19]

[11] Patent Number: 6,140,356
[45] Date of Patent: Oct. 31, 2000

[54] OPTHALMIC PHARMACEUTICAL COMPOSITIONS COMPRISING A NITRONE COMPOUND AND METHODS FOR TREATING OCULAR INFLAMMATION USING SUCH COMPOSITIONS

[75] Inventors: Kenneth W. Narducy, San Jose; Efraim Duzman, Irvine; John Michael Carney, Saratoga; Allan Lee Wilcox, Mountain View, all of Calif.

[73] Assignee: Centaur Pharmaceuticals, Inc., Sunnyvale, Calif.

[21] Appl. No.: 09/399,733

[22] Filed: Sep. 20, 1999

Related U.S. Application Data

[62] Division of application No. 08/847,386, Apr. 23, 1997, Pat. No. 5,972,977.
[60] Provisional application No. 60/016,276, Apr. 23, 1996.
[51] Int. Cl.$^7$ ............ A61K 31/15; A61K 31/16; A61K 31/165; A61K 31/235; A61K 31/415
[52] U.S. Cl. ............ 514/408; 514/529; 514/544; 514/617; 514/625; 514/640
[58] Field of Search ................ 514/529, 544, 514/617, 625, 640, 408

[56] References Cited

U.S. PATENT DOCUMENTS

| | | | |
|---|---|---|---|
| 4,153,722 | 5/1979 | Campbell et al. | 514/641 |
| 5,025,032 | 6/1991 | Carney et al. | 514/400 |
| 5,036,097 | 7/1991 | Floyd et al. | 514/400 |
| 5,527,828 | 6/1996 | Janzen et al. | 514/579 |
| 5,532,277 | 7/1996 | Janzen et al. | 514/579 |

FOREIGN PATENT DOCUMENTS

| | | |
|---|---|---|
| WO 91/05552 | 5/1991 | WIPO . |
| WO 92/22290 | 12/1992 | WIPO . |
| WO 95/11227 | 4/1995 | WIPO . |

OTHER PUBLICATIONS

Chan C, Ni M, Miele L, Cordella–Miele E, Ferrick M, Mukherjee A, and Nussenblatt R., Effects of Antiflammins on Endotoxin–induced Uveitis in Rats, *Arch Ophthalmal*109, 278–281 (1991).

Goto H, Wu GS, Chen F, Kristeva M, Sevanian A, And Rao NA., Lipid Peroxidation in Experimental Uveitis: Sequential Studies, *Curr Eye Res*, 11(6), 489–499 (1992).

Goto H., Retinal Tissue Damage and Lipid Peroxidation in Experimental Autoimmune Uveoretinitis, *Nippon Ganka Gakka Zasshi*, 95, 455–461 (1991).

Hu S, Li S, Pan S, Xie C, Huang X and Mao W., Effect of Superoxide Dismutase on Experimental Allergic Uveitis, *Yen Ko Hsueh Poa*, 9, 103–105 (1993).

Kasner L, Chan C, Cordella–Miele E, and Gery, I., The Effect of Chlorpromazine on Endotoxin Induced Uveitis in the Lewis Rat, *Curr Eye Res*, 11(9), 843–848 (1992).

Nussenblatt RB, Rodrigues MM, Wacker WB, Cevario SJ, and Salinas–Carmona MC., Cylosporin A: Inhibition of Experimental Autoimmune Uveitis in Lewis Rats, *J. Clin Invest*, 67, 1228–1231 (1981).

Nussenblatt R, Caspi R, Mahdi R, Chan C, Roberge F, Lider O, and Weiner H., Inhibition of S–antigen Induced Experimental Autoimmune Uveoretinitis by Oral Induction of Tolerance with S–antigen, *J Immunol*, 144, 1689–1695 (1990).

Parks DJ, Cheung MK, Chan CC, and Roberge FG., The Role of Nitric Oxide in Uveitis, *Arch Ophthalmol*, 112, 544–546 (1994).

(List continued on next page.)

*Primary Examiner*—Alan L. Rotman
*Attorney, Agent, or Firm*—Burns, Doane, Swecker & Mathis, LLP

[57] ABSTRACT

Ophthalmic pharmaceutical compositions containing a pharmaceutically acceptable ophthalmic carrier and an inflammation-treating amount of a nitrone compound are disclosed. Also disclosed are methods for treating ocular inflammation conditions, such as uveitis, using pharmaceutical compositions.

29 Claims, 1 Drawing Sheet

OTHER PUBLICATIONS

Rao NA, Patchett R, Fernandez MA, Sevanian A, Kunkel SL, and Marak GE., Treatment of Experimental Granulomatous Uveitis by Lipoxygenase and Cyclooxygenase Inhibitors, *Arch Ophthalmol*, 105, 413–415 (1987).

Rao N., Role of Oxygen Free Radicals in Retinal Damage Associated with Experimental Uveitis, *Tr Am Ophth Soc*, 88, 797–850 (1990).

Ruiz–Moreno J, Misiuk–Hojlo M, Thillaye B, and de Kozak Y., Suppression of Experimental Autoimmune Uveoretinitis. by Prazosin, an $\alpha_1$–adrenergic, *Curr Eye Res*, 11 suppl, 135–140 (1992).

Tilton RG, Chang K, Corbett JA, Misko TP, Currie MG, Bora NS, Kaplan HJ, and Williamson JR., Endotoxin–induced Uveitis in the Rat is Attenuated by Inhibition of Nitric Oxide Production, *Invest Ophthalmol Vis Sci*, 35(8), 3278–3288 (1994).

Uchio E, Kijima M, Tanaka S and Ohno S., Suppression of Experimental Uveitis with Monoclonal Antibodies to ICAM–1 and LFA–1, *Invest Ophthalmol Vis Sci*, 35, 2626–2631 (1994).

Wu GS, Sevanian A. and Rao NA., Detection of Retinal Lipid Hydroperoxides in Experimental Uveitis, *Free Radical Biol Med*, 12, 19–27 (1992).

Wu GS, Goto H, Sevanian A, and Rao NA., Generation of Chemiluminescence in Experimental Autoimmune Uveitis, *Curr Eye Res*,10, 909–917 (1991).

Wu GS, Walker J, and Rao NA., Effect of Deferoxamine on Retinal Lipid Peroxidation in Experimental Uveitis, *Invest Ophthalmol Vis Sci*, 34, 3084–3089 (1993).

OPTHALMIC PHARMACEUTICAL COMPOSITIONS COMPRISING A NITRONE COMPOUND AND METHODS FOR TREATING OCULAR INFLAMMATION USING SUCH COMPOSITIONS

This application is a division of 08/847,386 filed Apr. 23, 1997 now U.S. Pat. No. 5,972,977 which claims benefit to U.S. provisional application 60/016,276 filed Apr. 23, 1996.

BACKGROUND OF THE INVENTION

1. Field of the Invention

This invention relates to the treatment of ocular inflammation such as uveitis. More particularly, this invention relates to pharmaceutical compositions comprising a nitrone compound and methods for treating ocular inflammation using such compositions.

2. State of the Art

Uveitis is an inflammation of the uvea, the middle layer of tissue behind the white of the eye. This condition is sight-threatening and causes about 10 percent of the blindness in the United States. The cause of uveitis is poorly understood, but a variety of systemic diseases are associated with it. In at least one form of uveitis, free radicals have been demonstrated to be part of the disease process.

Corticosteroids, such as dexamethasone, are currently used to treat uveitis. However, the prolonged use of corticosteroids to treat such inflammation is associated with ocular hypertension and/or glaucoma. Accordingly, a need exists for novel pharmaceutical compositions which safely and effectively treat ocular inflammation conditions, such as uveitis.

It has now been discovered that certain nitrones compounds are useful for treating ocular inflammation, especially inflammation of the outer and middle eye, such as uveitis. The nitrone compounds useful for this purpose include, for example, α-(phenyl)-N-tert-butylnitrone (PBN), 5,5-dimethylpyrroline-N-oxide (DMPO) and α-(4-pyridyl 1-oxide)-N-tert-butyl nitrone (POBN) and derivatives thereof.

Nitrone compounds have been previously reported to be useful as therapeutics. See, for example, U.S. Pat. Nos. 5,025,032; 5,036,097; 5,527,828; 5,532,277 and 5,445,272; and published PCT Patent Application Nos. WO 91/05552 and WO 92/22290. Nitrone compounds, such as PBN, have also been used as analytical reagents for detecting highly reactive free radicals using electron spin resonance (ESR). See, for example, *Bull. Chem. Soc. Jpn.*, 1994, 67, 165; *Appl. Magn. Reson.*, 1992, 3, 1021; and *Aldrichimica Acta*, 1979, 12, 23.

References

The following additional references are related to uveitis and its treatment:

1. Nussenblatt R B, Rodrigues M M, Wacker W B, Cevario S J, and Salinas-Carmona M C. Cylosporin A: Inhibition of experimental autoimmune uveitis in Lewis rats. *J Clin Invest*, 67, 1228–1231 (1981).
2. Nussenblatt R, Caspi R, Mahdi R, Chan C, Roberge F, Lider O, and Weiner H. Inhibition of S-antigen induced experimental autoimmune uveoretinitis by oral induction of tolerance with S-antigen. *J Immunol*, 144, 1689–1695 (1990).
3. Chan C, Ni M, Miele L, Cordella-Miele E, Ferrick M, Mukherjee A, and Nussenblatt R. Effects of antiflammins on endotoxin-induced uveitis in rats. *Arch Ophthalmal*, 109, 278–281 (1991).
4. Rao N A, Patchett R, Fernandez M A, Sevanian A, Kunkel S L, and Marak G E. Treatment of experimental granulomatous uveitis by lipoxygenase and cyclo-oxygenase inhibitors. *Arch Ophthalmol*, 105, 413–415 (1987).
5. Rao N. Role of oxygen free radicals in retinal damage associated with experimental uveitis. *Tr Am Ophth Soc*, 88, 797–850 (1990).
6. Wu G S, Goto H, Sevanian A, and Rao N A. Generation of chemiluminescence in experimental autoimmune uveitis. *Curr Eye Res*, 10, 909–917 (1991).
7. Wu G S, Sevanian A. and Rao N A. Detection of retinal lipid hydroperoxides in experimental uveitis. *Free Radical Biol Med*, 12, 19–27 (1992).
8. Goto H, Wu G S, Chen F, Kristeva M, Sevanian A, and Rao N A. Lipid peroxidation in experimental uveitis: sequential studies. *Curr Eye Res*, 11, 489–499 (1992).
9. Wu G S, Walker J, and Rao N A. Effect of deferoxamine on retinal lipid peroxidation in experimental uveitis. *Invest Ophthalmol Vis Sci*, 34, 3084–3089 (1993).
10. Ruiz-Moreno J, Misiuk-Hojlo M, Thillaye B, and de Kozak Y. Suppression of experimental autoimmune uveoretinitis. by prazosin, an α1-adrenergic. *Curr Eye Res*, 11 suppl, 135–140 (1992).
11. Kasner L Chan C, Cordella-Miele E, and Gery, I. The effect of chlorpromazine on endotoxin induced uveitis in the Lewis rat. *Curr Eye Res*, 11, 843–848 (1992).
12. Goto H. Retinal tissue damage and lipid peroxidation in experimental autoimmune uveoretinitis. *Nippon Ganka Gakka Zasshi*, 95, 455–461 (1991).
13. Hu S, Li S, Pan S, Xie C, Huang X and Mao W. Effect of superoxide dismutase on experimental allergic uveitis. *Yen Ko Hsueh Pao*, 9, 103–105 (1993).
14. Parks D J, Cheung M K, Chan C C, and Roberge F G. The role of nitric oxide in uveitis. *Arch Ophthalmol*, 112, 544–546 (1994).
15. Tilton R G, Chang K, Corbett J A, Misko T P, Currie M G, Bora N S, Kaplan H J, and Williamson J R. Endotoxin-induced uveitis in the rat is attenuated by inhibition of nitric oxide production. *Invest Ophthalmol Vis Sci*, 35, 3278–3288 (1994).
16. Uchio E, Kijima M, Tanaka S and Ohno S. Suppression of experimental uveitis with monoclonal antibodies to ICAM-1 and LFA-1. *Invest Ophthalmol Vis Sci*, 35, 2626–2631 (1994).

SUMMARY OF THE INVENTION

It has now been found that certain nitrone compounds are useful for treating ocular inflammation, especially inflammation of the outer and middle eye such as uveitis. Several of the nitrone compounds employed in this invention have novel chemical compositions.

Accordingly, in one of its composition aspects, this invention is directed to an ophthalmic pharmaceutical composition comprising a pharmaceutically acceptable ophthalmic carrier and an ocular inflammation-treating amount of 5,5-dimethylpyrroline-N-oxide or a compound of formula I:

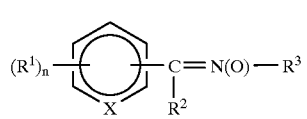

I wherein
each $R^1$ is independently selected from the group consisting of alkyl, lower alkoxy, aminoacyl, acyloxy, hydroxy and —CO₂Y, wherein Y is hydrogen or a pharmaceutically acceptable salt;

R² is selected from the group consisting of hydrogen, alkyl and aryl;

R³ is selected from the group consisting of alkyl, alkenyl, alkynyl, aryl, alkaryl, alkcycloalkyl, cycloalkyl and cycloalkenyl;

X is CH or N→O; and n is an integer from 0 to 3.

Preferably, each R¹ is independently selected from the group consisting of alkyl, lower alkoxy and hydroxy.

R² is preferably hydrogen or alkyl. More preferably, R² is hydrogen.

Preferably, R³ is selected from the group consisting of alkyl, alkaryl, aryl and cycloalkyl. More preferably, R³ is alkyl or cycloalkyl. Still more preferably, R³ is alkyl. An especially preferred alkyl group is tert-butyl.

In formula I above, X is preferably CH, i.e., the aryl ring is a phenyl or substituted phenyl ring. Examples of preferred substituted phenyl rings include, but are not limited to, 3,5-dimethoxy-4-hydroxyphenyl, 3,5-di-tert-butyl-4-hydroxyphenyl and 2-hydroxyphenyl.

In the ophthalmic pharmaceutical composition of this invention, the ophthalmic carrier is preferably a sterile aqueous carrier or a salve or ointment carrier. In a preferred embodiment, the ophthalmic pharmaceutical composition employing a sterile aqueous carrier further comprises one or more additives selected from the group consisting of benzalkonium chloride and thimerosal.

In another of its composition aspects, this invention is directed to an ophthalmic pharmaceutical composition comprising a pharmaceutically acceptable ophthalmic carrier and an ocular inflammation-treating amount of a compound selected from the group consisting of:

α-(phenyl)-N-tert-butylnitrone

α-(3,5-dimethoxy-4-hydroxyphenyl)-N-tert-butylnitrone

α-(3,5-di-tert-butyl-4-hydroxyphenyl)-N-tert-butylnitrone

α-(2-hydroxyphenyl)-N-tert-butylnitrone

α-(2,4,6-trihydroxyphenyl)-N-tert-butylnitrone

α-(4-pyridyl 1-oxide)-N-tert-butylnitrone

α-(4-pyridyl 1-oxide)-N-n-propylnitrone, and 5,5-dimethylpyrroline-N-oxide.

Still further, this invention provides novel compounds selected from the group consisting of:

α-(3,5-dimethoxy-4-hydroxyphenyl)-N-tert-butylnitrone

α-(2,4,6trihydroxyphenyl)-N-tert-butylnitrone, and

α-(4-pyridyl 1-oxide)-N-n-propylnitrone.

Additionally, this invention provides pharmaceutical compositions comprising a pharmaceutically acceptable inert carrier and an inflammation-treating amount of a compound selected from the group consisting of:

α-(3,5-dimethoxy-4-hydroxyphenyl)-N-tert-butylnitrone

α-(2,4,6trihydroxyphenyl)-N-tert-butylnitrone, and

α-(4-pyridyl 1-oxide)-N-n-propylnitrone.

In one of its method aspects, this invention is directed to a method for treating a mammal with ocular inflammation which method comprises administering to said mammal a pharmaceutical composition comprising a pharmaceutically acceptable inert carrier and an ocular inflammation-treating amount of 5,5-dimethylpyrroline-N-oxide or a compound of formula I:

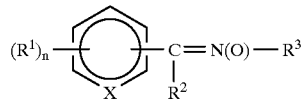

wherein each R¹ is independently selected from the group consisting of alkyl, lower alkoxy, aminoacyl, acyloxy, hydroxy and —CO₂Y, wherein Y is hydrogen or a pharmaceutically acceptable salt;

R² is selected from the group consisting of hydrogen, alkyl and aryl;

R³ is selected from the group consisting of alkyl, alkenyl, alkynyl, aryl, alkaryl, alkcycloalkyl, cycloalkyl and cycloalkenyl;

X is CH or N→O; and n is an integer from 0 to 3.

In another of its method aspects, this invention is directed to a method for treating a mammal with inflammation which method comprises administering to said mammal a pharmaceutical composition comprising a pharmaceutically acceptable inert carrier and an inflammation-treating amount of a compound selected from the group consisting of:

α-(3,5-dimethoxy-4-hydroxyphenyl)-N-tert-butylnitrone

α-(2,4,6-trihydroxyphenyl)-N-tert-butylnitrone, and

α-(4-pyridyl 1-oxide)-N-n-propylnitrone.

DETAILED DESCRIPTION OF THE INVENTION

Figure 1:
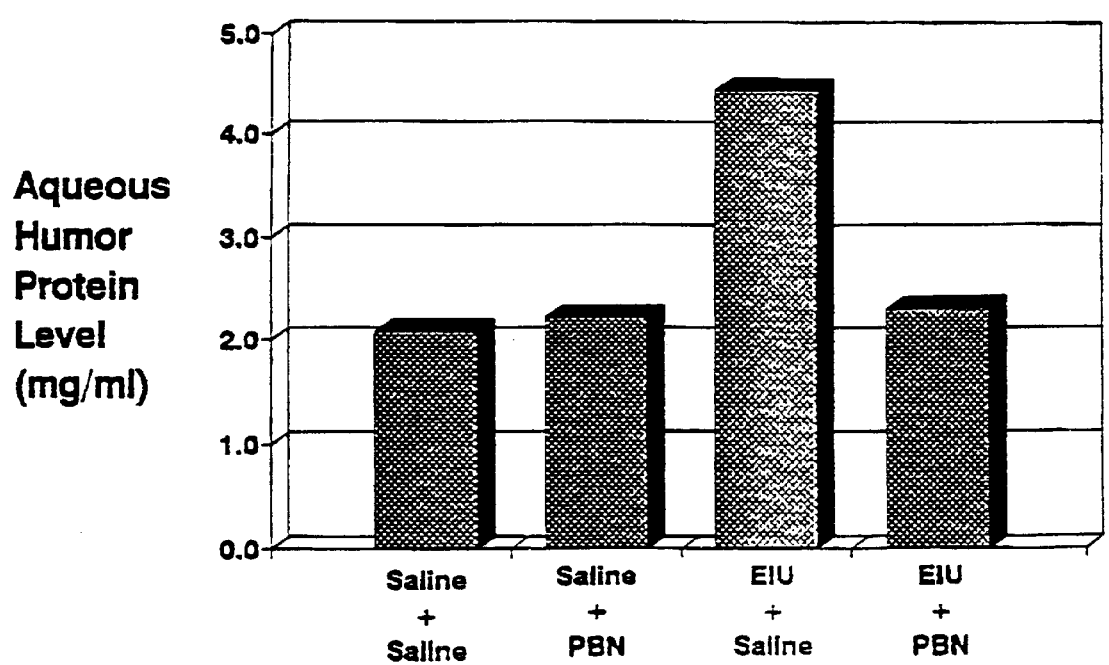
FIG. 1 is a bar graph comparing the aqueous humor protein level (mg/mL) in rats with endotoxin-induced uveitis (EIU) treated with N-tert-butyl-α-phenylnitrone (PBN) or a saline control. The aqueous humor protein level for control rats treated with PBN or a saline solution are also shown.

As discussed above, the ophthalmic pharmaceutical compositions of this invention contain one or more nitrone compounds as the active component(s). Prior to describing this invention in further detail, the following terms will first be defined.

Definitions

"Alkyl" refers to monovalent alkyl groups preferably having from 1 to about 12 carbon atoms, more preferably 1 to 8 carbon atoms and still more preferably 1 to 5 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to alkyl groups having 1 to 5 carbon atoms.

"Alkylene" refers to divalent alkylene groups preferably having from 1 to 10 carbon atoms and more preferably 1 to 6 carbon atoms which can be straight chain or branched. This term is exemplified by groups such as methylene (—CH₂—), ethylene (—CH₂CH₂—), the propylene isomers (e.g., —CH₂CH₂CH₂— and —CH(CH₃)CH₂—) and the like.

"Alkenylene" refers to divalent alkenylene groups preferably having from 2 to 10 carbon atoms and more preferably 2 to 6 carbon atoms which can be straight chain or branched and having at least 1 and preferably from 1–2 sites of alkenyl unsaturation. This term is exemplified by groups such as ethenylene (—CH=CH—), the propenylene isomers (e.g., —CH═CHCH$_2$— and —C(CH$_3$)═CH— and —CH═C(CH$_3$)—) and the like.

"Alkaryl" refers to -alkylene-aryl groups preferably having from 1 to 10 carbon atoms in the alkylene moiety and from 6 to 14 carbon atoms in the aryl moiety. Such alkaryl groups are exemplified by benzyl, phenethyl, and the like.

"Alkcycloalkyl" refers to -alkylene-cycloalkyl groups preferably having from 1 to 10 carbon atoms in the alkylene moiety and from 3 to 8 carbon atoms in the cycloalkyl moiety. Such alkcycloalkyl groups are exemplified by —CH$_2$-cyclopropyl, —CH$_2$-cyclopentyl, —CH$_2$CH$_2$-cyclohexyl, and the like.

"Alkoxy" refers to the group "alkyl-O-". Preferred alkoxy groups include, by way of example, methoxy, ethoxy, n-propoxy, isopropoxy, n-butoxy, tert-butoxy, sec-butoxy, n-pentoxy and the like. The term "lower alkoxy" refers to alkyl groups having 1 to 5 carbon atoms.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH═CH$_2$), n-propenyl (—CH$_2$CH═CH$_2$), isopropenyl (—C(CH$_3$)═CH$_2$), and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—CH≡CH$_2$), propargyl (—CH$_2$CH≡CH$_2$), and the like.

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 3 substituents selected from the group consisting of alkyl, alkoxy, aminoacyl, acyloxy, hydroxy, and the like.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Pharmaceutically acceptable salt" refers to pharmaceutically acceptable salts which are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically acceptable cation" refers to a pharmaceutically acceptable cationic counterion of an acidic functional group. Such cations are exemplified by sodium, potassium, calcium, magnesium, ammonium, tetraalkylammonium cations, and the like.

Nitrone Compounds

Preferred nitrone compounds for use in the pharmaceutical compositions of this invention include α-(phenyl)-N-tert-butylnitrone (PBN), 5,5-dimethylpyrroline-N-oxide (DMPO) and α-(4-pyridyl 1-oxide)-N-tert-butylnitrone (POBN) and derivatives thereof. Particularly preferred derivatives of these compounds including hydroxy derivatives, such as α-(2-hydroxyphenyl)-N-tert-butylnitrone, α-(3-hydroxyphenyl)-N-tert-butylnitrone and α-(4-hydroxyphenyl)-N-tert-butylnitrone; dihydroxy and trihydroxy derivatives, such as α-(2,4,6-trihydroxyphenyl)-N-tert-butylnitrone; esters derivatives, especially esters which release 2-, 3-, or 4-hydroxy derivatives, such as α-(2-acetoxyphenyl)-N-tert-butylnitrone, α-(3-acetoxyphenyl)-N-tert-butylnitrone and α-(4-acetoxyphenyl)-N-tert-butylnitrone; carboxyl derivatives, such as α-(2-carboxyphenyl)-N-tert-butylnitrone, α-(3-carboxyphenyl)-N-tert-butylnitrone and α-(4-carboxyphenyl)-N-tert-butylnitrone; and acetamido derivatives, such as α-(2-acetamidophenyl)-N-tert-butylnitrone, α-(3-acetamidophenyl)-N-tert-butylnitrone and α-(4-acetamidophenyl)-N-tert-butylnitrone. Other preferred compounds include diphenyl nitrone (PPN) and the analogous diphenyl nitrone derivatives; α-(3,5-dimethoxy-4-hydroxyphenyl)-N-tert-butylnitrone; α-(2,4,6trihydroxyphenyl)-N-tert-butylnitrone; and α-(4-pyridyl 1-oxide)-N-n-propylnitrone.

A particularly preferred group of nitrone compounds for use in this invention are those having formula I:

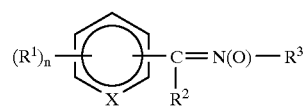

wherein
  each $R^1$ is independently selected from the group consisting of alkyl, lower alkoxy, aminoacyl, acyloxy, hydroxy and —CO$_2$Y, wherein Y is hydrogen or a pharmaceutically acceptable salt;
  $R^2$ is selected from the group consisting of hydrogen, alkyl and aryl;
  $R^3$ is selected from the group consisting of alkyl, alkenyl, alkynyl, aryl, alkaryl, alkcycloalkyl, cycloalkyl and cycloalkenyl;
  X is CH or N→O; and
  n is an integer from 0 to 3.

It will be appreciated that some of the above compounds can exist as salts, i.e., the carboxyl derivatives. In such cases, the compounds may be ionized and accompanied by a pharmaceutically acceptable anion or cation as appropriate. Most commonly, a cation is a monovalent material such as sodium, potassium or ammonium, but it can also be a multivalent cation in combination with a pharmaceutically acceptable monovalent anion, for example calcium with a chloride, bromide, iodide, hydroxyl, nitrate, sulfonate, acetate, tartrate, oxalate, succinate, palmoate or the like anion; magnesium with such anions; zinc with such anions or the like.

Mixtures of two or more nitrone compounds may be employed, if desired, in the pharmaceutical compositions and methods of this invention.

General Synthetic Procedures

The nitrone compounds employed in this invention are either commercially available or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protecting and deprotecting various functional groups are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

In a preferred method of synthesis, the nitrone compounds employed in this invention are prepared by coupling a carbonyl compound of formula II:

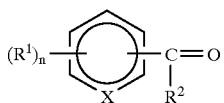

II wherein $R^1$, $R^2$, X, and n are as defined above, with a hydroxylamine of formula III:

III wherein $R^3$ is as defined above, under conventional reaction conditions.

The coupling reaction is typically conducted by contacting the carbonyl compound II with at least one equivalent, preferably about 1.1 to about 2 equivalents, of hydroxylamine III in an inert polar solvent such as water, methanol, ethanol, 1,4-dioxane, tetrahydrofuran, dimethylsulfoxide, dimethylformamide and the like. This reaction is preferably conducted at a temperature of from about 0° C. to about 100° C. for about 1 to about 48 hours. Optionally, a catalytic amount of an acid, such as acetic acid, p-toluenesulfonic acid and the like, may be employed in this reaction. Upon completion of the reaction, the nitrone compound of formula I is recovered by conventional methods including precipitation, chromatography, filtration, distillation and the like.

The carbonyl compounds of formula II employed in the coupling reaction are either known compounds or can be prepared from known compounds by conventional procedures. Preferred carbonyl compounds include, but are not limited to, benzaldehyde, 2-hydroxybenzaldehyde, 3-hydroxybenzaldehyde, 4-hydroxybenzaldehyde, 2,4,6-trihydroxybenzaldehyde, 3,5-di-tert-butyl-4-hydroxybenzaldehyde, 3,5-dimethoxy-4-hydroxybenzaldehyde, 4-formylpyridine-1-oxide and the like.

The hydroxylamine compounds of formula III above are also known compounds or compounds which can be prepared from known compounds by conventional procedures. Typically, the hydroxylamine compounds of formula III are prepared by reduction of the corresponding nitro compound (i.e., $R^3$—$NO_2$, wherein $R^3$ is as defined above) using a suitable catalyst such as an activated zinc/acetic acid catalyst or an aluminum/mercury amalgam catalyst. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc catalyst or an ether/water mixture in the case of the aluminum amalgam catalyst. Aliphatic nitro compounds (in the form of their salts) can also be reduced to hydroxylamines using borane in tetrahydrofuran. Since some hydroxylamines have limited stability, such compounds are generally prepared immediately prior to reaction with the carbonyl compound of formula II.

Preferred hydroxylamines for use in this invention include, but are not limited to, N-methylhydroxylamine, N-etbylhydroxylamine, N-n-propylhydroxylamine, N-isopropylhydroxylamine, N-n-butylhydroxylamine, N-isobutylhydroxylamine, N-sec-butylhydroxylamine, N-tert-butylhydroxylamine, N-n-pentylhydroxylamine, N-cyclopentylhydroxylamine, N-n-hexylhydroxylamine, N-cyclohexylhydroxylamine, N-n-octylhydroxylamine, N-tert-octylhydroxylamine, N-phenylhydroxylamine and the like. Especially preferred is N-tert-butylhydroxylamine.

Pharmaceutical Compositions

The nitrone compounds (including salts thereof) employed in this invention are preferably formulated into ophthalmic pharmaceutical compositions suitable for topical administration.

Topical formulations can include topical ocular liquids comprising one or more nitrone compound dissolved or suspended in sterile, isotonic, usually aqueous pharmaceutically acceptable ocular vehicles. Topical formulations can also be prepared in the form of salves or ointments. Such salves or ointments typically comprise one or more nitrone compound dissolved or suspended in a sterile pharmaceutically acceptable salve or ointment base, such as a mineral oil-white petrolatum base.

Topical formulations can include from about 0.01% by weight to about 10% by weight of the active nitrone compound with the remainder of the formulation being the carrier and other materials known in the art as topical pharmaceutical components. Such additional components may include buffers, surfactants, solubilizers, preservatives, emulsifying agents, isotonizers, stablilizers, pH adjusting agents and the like.

Preferred additives for use in sterile, isotonic solutions include, but are not limited to, benzalkonium chloride, thimerosal, chlorobutanol, sodium chloride, boric acid and mixtures thereof. In a preferred embodiment, benzalkonium chloride is added as an antimicrobial preservative in an amount ranging from about 0.001 to about 0.02 weight percent, preferably 0.01 weight percent. In another preferred embodiment, thimerosal is added as an antimicrobial preservative in an amount ranging from about 0.005 to about 0.02 weight percent. In salve or ointment compositions, anhydrous lanolin may also be included in the formulation. Thimerosal or chlorobutanol are also preferably added to such ointment compositions as antimicrobial agents.

Alternatively, systemic formulations of the nitrone compounds may also be used to treat ocular inflammation. Such systemic formulations can be administered by a variety of routes including oral, transdermal, subcutaneous, intravenous, intramuscular, and intranasal. Depending on the intended route of delivery, the compounds of this invention are preferably formulated as either injectable or oral compositions.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the nitrone compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the nitrone compound in such compositions is typically a minor component, typically ranging from about 0.05 to 10% by weight with the remainder being the injectable carrier and the like.

The above described components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The nitrone compounds employed in this invention can also be administered in sustained release forms or from sustained release drug delivery systems. A description of representative sustained release materials can be found in the incorporated materials in *Remington's Pharmaceutical Sciences*.

The following formulation examples illustrate representative pharmaceutical compositions suitable for systemic delivery of the nitrone compounds used in this invention. The present invention, however, is not limited to the following exemplified pharmaceutical compositions.

Formulation 1—Eye Drops

A nitrone compound, such as PBN (0.5 g), boric acid (1.8 g), benzalkonium chloride (0.005 g) are mixed to dissolve in purified sterile water. The pH of the solution is adjusted with 1N sodium hydroxide to about 7.3. Purified sterile water is then added to produce a total volume of 100 mL and the solution sterilized by filtration.

Formulation 2—Ophthalmic Ointment

A nitrone compound, such as PBN, is admixed with mineral oil and white petrolatum to form an ointment containing 0.05 weight percent active nitrone compound.

Formulation 3—Oral Tablets

A nitrone compound, such as PBN, is admixed as a dry powder with a dry gelatin binder in an approximate 1:10 weight ratio. A minor amount of magnesium stearate is added as a lubricant. The mixture is formed into 240–270 mg tablets (20–30 mg of active nitrone compound per tablet) in a tablet press.

Formulation 4—Oral Capsules

A nitrone compound, such as PBN, is admixed as a dry powder with a starch diluent in an approximate 1:4 weight ratio. The mixture is filled into 250 mg capsules (50 mg of active nitrone compound per capsule).

Formulation 5—Liquid Solution

A nitrone compound, such as DMPO (50 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 6—Injection

A nitrone compound, such as PBN, is dissolved in a buffered sterile saline injectable aqueous medium to a concentration of approximately 5 mg/ml.

It will be appreciated that any of the nitrone compounds described herein could be employed in any of these representative formulations taking into account solubility, dispersibility and the like, and that any of these formulations could be administered in any of the above described manners so as to treat ocular inflammation.

Conditions Treated and Treatment Regimens

The conditions treated with the ophthalmic pharmaceutical compositions of this invention generally include ocular inflammation and the various symptoms which fall within the ocular inflammation definition. These include, for example, uveitis. The nitrone-containing formulations provided by this invention can be administered to achieve an inflammation-reducing effect in the eye. To achieve this effect, a topical preparation is administered directly to the inflamed eye by instilling adequate topical solution or salve or ointment to the inflamed eye to reduce the inflammation. Typically, a suitable dose ranges from about 0.001 mg/kg to about 10 mg/kg. This can be a single dose but more typically, a series of from 2 to 5 doses per day is administered over the course of the disease. Systemic administration of the pharmaceutical compositions can be at levels of from about 0.001 to about 100 mg/kg per dose with from 1 to about 5 doses being administered daily so as to achieve an overall dosing level of from about 0.001 mg/kg/hour to about 10 mg/kg/hour for from about 1 to about 120 hours and especially from 1 to 96 hours.

In any treatment regimen, a health care professional should assess the patient's condition and determine whether or not the patient would benefit from nitrone treatment. Some routine dosage adjustments may be necessary to achieve an optimal dosing level and pattern.

The compounds of this invention can be administered as the sole active agent or they can be administered in combination with other agents, including other active nitrone compounds.

It will be understood that the novel nitrone compounds provided by this invention, including α-(3,5-dimethoxy-4-hydroxyphenyl)-N-tert-butylnitrone, α-(2,4,6-trihydroxyphenyl)-N-tert-butylnitrone, and α-(4-pyridyl 1-oxide)-N-n-propylnitrone, have other pharmaceutical applications related to their anti-inflammatory properties when such compounds are admininistered systemically, preferably orally or parenterally, in doses ranging from about 0.001 to about 100 mg/kg per dose with from 1 to about 5 doses being administered daily so as to achieve an overall dosing level of from about 0.001 mg/kg/hour to about 10 mg/kg/hour for from about 1 to about 120 hours and especially from 1 to 96 hours.

EXAMPLES

The following synthetic and biological examples are offered to illustrate this invention and are not to be construed in any way as limiting the scope of this invention.

Example 1

Synthesis of α-(3,5-Dimethoxy-4-hydroxyphenyl)-N-tert-butylnitrone

Syringealdehyde (5.47 g, 0.030 mole) was dissolved in refluxing benzene (100 mL) and a solution of N-tert-butyl hydroxylamine (2.67 g, 0.030 mole) in 50 mL benzene was added dropwise. The reaction was allowed to stand overnight at room temperature then filtered, solvent stripped, and the residue washed with ethyl acetate to give a pale-green powder (1.54 g, 20.3% yield). The product had a melting point of 163–164° C. and an Rf on silica gel TLC (100% ethyl acetate) of 0.27 (syringealdehyde Rf=0.75).

Spectroscopic data was as follows:

$^1$H NMR (CDCl$_3$): δ=7.703 ppm (s, 2H, aryl 2,6-H's), 7.454 ppm (s, 1H, nitronyl-H), 5.290 ppm (s, 1H, phenoxyl-H), 3.933 ppm (s, 6H, CH3O—), 1.611 ppm (s, 9H, t-butyl-CH3).

$^{13}$C NMR (CDCl$_3$): δ=146.80 ppm (aryl 3,5-C), 137.16 ppm (aryl 4-C), 129.93 ppm (nitronyl-C), 122.83 ppm (aryl 1-C), 106.95 ppm (aryl 2,6-C), 70.42 ppm (C(CH3)3), 56.50 (CH3O—), 28.41 ppm (C(CH3)3).

Example 2

Synthesis of α-(2,4,6-Trihydroxyphenyl)-N-tert-butylnitrone 2,4-6-Trihydroxybenzaldehyde (17.69 g, 0.115 mole) was added to a solution of N-tert-butyl hydroxylamine (14.32 g, 0.161 mole) in benzene (250 mL). p-Toluenesulfonic acid (15 mg) was added and the reaction vessel fitted with a Dean-Stark trap. The reaction was heated at reflux for 88 hours under nitrogen and then diluted with 500 mL of ethyl acetate. The solution was washed with water, brine and dried over sodium sulfate. The product was recrystallized from ethanol/water and then dried in vacuo for 2 hr at 35° C. to provide 16.95 g (65.5% yield) of the title compound. The product had a melting point of 189.9–190.3° C. and an Rf on silica gel TLC (50% hexane, 45% ethyl acetate, 5% methanol) of 0.31 (2,4,6-trihydroxybenzaldehyde Rf=0.47).

Spectroscopic data was as follows:

$^1$H NMR (DMSO-d$_6$): δ=11.88 ppm (s, 0.2H, phenoxyl-H), 9.801 ppm (s, 0.8 H, phenoxyl-H), 7.948 ppm (s, 1H, nitronyl-H), 5,746 ppm (s, 2H, aryl 3,5-H's), 1.497 ppm (s, 9H, t-butyl-CH3).

$^{13}$C NMR (DMSO-d$_6$): δ=164.48 ppm (aryl 4-C), 161.93 ppm (aryl 2,6-C), 133.91 ppm (nitronyl-C), 99.15 ppm (aryl 1-C), 95.46 ppm (aryl 3,5-C), 68.61 ppm (C(CH3)3), 27.82 ppm (C(CH3)3).

FTIR (KBr Pellet): 3465 cm$^{-1}$ (O—H stretch), 2983 cm$^-$ (C—H aliphatic stretch), 1626 cm$^{-1}$ (C=N stretch), 1173 cm$^-$ (N—O stretch).

Example 3

Synthesis of α-(4-Pyridyl 1-oxide)-N-n-propylnitrone

N-n-Propyl hydroxylamine (1.62 g, 0.021 mole) in 40 mL methanol was added to pyridine-4-carboxaldehyde 1-N-oxide (2.21 g, 0.018 mole) in methanol (40 mL). Conc. HCl (3 drops) was added and the reaction was heated at reflux for 16 hours, solvent stripped, and the residue washed with hexane to afford 3.20 g (98% yield) of the title compound. The product had a melting point of 113.1–115.5° C.

Spectroscopic data was as follows:

$^1$H NMR (CDCl$_3$): δ=8.142 ppm (s, 4 H, aryl-H), 7.384 ppm (s, 1H, nitronyl-H), 3.915 ppm (t, J=7.0 Hz, 2H, propyl H's), 2.017 ppm (q. J=7.3 Hz, 2H, propyl H's), 1.005 ppm (t, J=7.3 Hz, 3H, propyl H's).

Example 4

Treatment of Endotoxin-Induced Uveitis

Administration of lipopolysaccharide (LPS) to experimental animals in sublethal dosages induces a characteristic inflammatory response localized to the anterior portion of the eye. This transient but intense neutrophilic response, termed endotoxin-induced uveitis (EIU), is used as a model for uveitis inflammation. The inflammatory response is measured by determining the protein level in the aqueous humor of the animals. In this example, the ability of α-(phenyl)-N-tert-butylnitrone (PBN) to effectively treat endotoxin-induced uveitis is demonstrated. PBN is commercially available from Aldrich, Milwaukee, Wis., U.S.A.

Female Lewis rats, 8–10 weeks old and weighing 170–200 g, were housed in a 12 hour light/dark cycle environment and fed rat chow ad libitum. All animal experiments adhered to the NIH Guiding Principles in the Care and Use of Animals. Endotoxin-induced uveitis (EIU) was developed in Lewis rats with a subcutaneous injection of 750 g/kg of LPS (endotoxin from *Escherichia coli* serotype 055:B5, Lot 34H4113, Sigma Chemical Co) in physiological saline, followed immediately by an intraperitoneal injection of (PBN) or a saline placebo. A second equivalent injection of PBN or placebo was made 6 hours later. LPS solutions were prepared such that 1 mL was given for each kg of rat body weight (e.g., for these 750 μg/kg experiments, the LPS solution contained 750 μg/mL). PBN was administered at 100 mg/kg body weight as a solution in saline (20 mg/mL). Animals were sacrificed by CO$_2$ inhalation 24 hours after LPS injection. Aqueous humor was withdrawn by pipet immediately after sacrifice and analyzed for protein content.

A protein assay was performed on samples of the aqueous humor aspirate by the method of Smith [P K Smith, et al., *Anal Biochem,* 150, 76 (1975)] using the BCA-1 Protein Determination Kit (Sigma Chemical Co). The aqueous humor samples were encoded in order to eliminate analyst bias. A 5 μL sample of the aqueous humor was withdrawn from each sample container and mixed with 95 μL of water in a test tube. Two mL of the protein determination reagent was then added to each tube. Each tube was vortexed and then incubated in a 37° C. water bath for 30 minutes. The tubes were cooled to room temperature. The absorbance at 562 nm was determined on a Cary spectrophotometer using water to zero the instrument. The amount of protein in the aqueous humor sample was calculated from the linear regression equation of a concomitantly determined standard curve.

The results from the experiments are shown in the Table 1 below and in FIG. 1. The data were analyzed by application of the Student's t-Test which showed that LPS+saline is significantly different from the blank (saline+saline), the negative control (saline+PBN), and the sample (LPS+PBN) with p<0.05 (see Table 1 below).

TABLE 1

Aqueous Humor Protein Content

| Treatment | Protein Content (mg/mL) | P(T < =t) two-tail vs. LPS + saline |
|---|---|---|
| saline + saline | 2.08 | <0.05 |
| saline + PBN | 2.23 | <0.05 |
| LPS + PBN | 2.31 | <0.05 |
| LPS + saline | 4.44 | NA |

The data in Table 1 demonstrate that LPS produces a significant level of inflammation as measured by aqueous humor protein content and that PBN effectively protects against endotoxin-induced uveitis.

Example 5

Treatment of Endotoxin-Induced Uveitis

In this example, the ability of various nitrone compounds to effectively treat endotoxin-induced uveitis is demonstrated. The nitrones used in this example were either commercially available or prepared using art-recognized procedures.

Acclimated male Lewis rats (Harlan Sprague Dawley, Inc., Indianapolis, Ind., U.S.A.) weighing between 200 and 250 grams were used in this experiment since this strain and gender of rat is genetically susceptible to endotoxin induced uveitis (EIU). Animals were housed 1–3 per cage for the duration of the study. The animals received Purina laboratory chow (Purina Rodent Diet 50-02, PMI Feeds, Inc., St. Louis, Mo., U.S.A.) and deionized water (18.2 mega-ohm, purified using a Milli Q water purification system, Millipore Corporation, Bedford, Mass., U.S.A.) ad libitum.

To induce EIU, lipopolysaccharide (LPS from *E. coli* serotype 055:B5, L-2880, Sigma Chemical Co., St. Louis, Mo., U.S.A.) diluted to 250 μg/mL saline was given as a 0.1 ml footpad injection at time 0. Immediately after the footpad injection of LPS, each rat received an ip or oral dose of the nitrone compound or the control vehicle. The nitrone compound or vehicle was administered again at 6 hours (except as indicated below). The standard concentration for nitrone administration was 100 mg/kg with a dose volume of 1 mL/kg. For comparison, dexamethasone and cyclosporin were also administered at 1 mg/kg ip and 75 mg/kg po, respectively.

After 24 hours, animals were sacrificed by $CO_2$ inhalation and 10 μL of aqueous humor was withdrawn from each eye using a 26 gauge needle (Hamilton, Co. Reno, Nev.). The two aqueous humor sample from a single animal were combined in a microcentrifuge tube with 50 μL of saline and kept on ice. Using a small aliquot of the diluted sample, cell counts were immediately made with a hemacytometer (Hausser Scientific, Horsahm, Pa., U.S.A.) and Nikon Diaphot 300 light microscope. Only living cells were counted.

The remaining aqueous humor samples were placed in a microcentrifuge (Fisher Scientific, Pittsburgh, Pa., U.S.A.) for 10 minutes at 3500 rpm. Protein content of the supernatant was determined using a Bicinchoninic Acid Protein kit (Sigma Chemical Co., St. Louis, Mo., U.S.A.) within 6 hours of initial sample collection.

Protein concentration and cell counts of treated and untreated animals were compared using Student's t-test. The percent protection provided by the test compounds compared to the untreated controls is shown in Table 2 below.

TABLE 2

Percent Protection Provided by Test Compounds

| No. | Test Compound | Percent Protection Protein | Percent Protection Cells | Statistics |
|---|---|---|---|---|
| 5A | α-(phenyl)-N-tert-butylnitrone | 29.20 | — | p < 0.05 |
| 5B | α-(4-pyridyl 1-oxide)-N-tert-butylnitrone | 75.40 | — | p < 0.05 |
| 5C | α-(3,5-dimethoxy-4-hydroxyphenyl)-N-tert-butylnitrone[1] | 71.30 | — | p < 0.001 |
| 5D | α-(3,5-di-tert-butyl-4-hydroxyphenyl)-N-tert-butylnitrone | 40.00 | 72.00 | p < 0.001 |
| 5E | α-(2-hydroxyphenyl)-N-tert-butylnitrone | 20.90 | — | N.S. |
| 5F | α-(4-pyridyl 1-oxide)-N-n-propylnitrone | 9.70 | — | N.S. |
| 5G | α-(2,4,6-trihydroxyphenyl)-N-tert-butylnitrone | 4.60 | — | N.S. |
| 5H | Dexamethasone | 65.90 | 99.00 | p < 0.01 |
| 5I | Cyclosporine | 46.60 | — | p < 0.05 |

[1]This compound was only administered once at time 0.

The data in Table 1 demonstrate that the nitrone compounds employed in the pharmaceutical compositions of this invention effectively protect against endotoxin-induced uveitis.

From the foregoing description, various modifications and changes in the compositions and methods of this invention will occur to those skilled in the art. All such modifications coming within the scope of the appended claims are intended to be included therein.

What is claimed is:

1. An ophthalmic pharmaceutical composition comprising a pharmaceutically acceptable ophthalmic carrier and an ocular inflammation-treating amount of a compound of formula I:

$$(R^1)_n - \underset{X}{\text{Ar}} - \underset{R^2}{C} = N(O) - R^3 \qquad I$$

wherein
each $R^1$ is independently selected from the group consisting of alkyl, lower alkoxy, aminoacyl, acyloxy, hydroxy and —$CO_2Y$, wherein Y is hydrogen or a pharmaceutically acceptable salt;
$R^2$ is selected from the group consisting of hydrogen, alkyl and aryl;
$R^3$ is selected from the group consisting of alkyl, alkenyl, alkynyl, aryl, alkaryl, alkcycloalkyl, cycloalkyl and cycloalkenyl;
X is CH; and
n is an integer from 0 to 3.

2. The ophthalmic pharmaceutical composition of claim 1 wherein each $R^1$ is independently selected from the group consisting of alkyl, lower alkoxy and hydroxy.

3. The ophthalmic pharmaceutical composition of claim 1 wherein $R^2$ is hydrogen.

4. The ophthalmic pharmaceutical composition of claim 1 wherein $R^3$ is selected from the group consisting of alkyl and cycloalkyl.

5. The ophthalmic pharmaceutical composition of claim 1 wherein $R^3$ is tert-butyl.

6. The ophthalmic pharmaceutical composition of claim 1 wherein the ophthalmic carrier is a sterile aqueous carrier.

7. The ophthalmic pharmaceutical composition of claim 6 wherein the composition further comprises one or more additives selected from the group consisting of benzalkonium chloride and thimerosal.

8. The ophthalmic pharmaceutical composition of claim 1 wherein the ophthalmic carrier is a salve or ointment carrier.

9. An ophthalmic pharmaceutical composition comprising a pharmaceutically acceptable ophthalmic carrier and an ocular inflammation-treating amount of a compound selected from the group consisting of:

α-(phenyl)-N-tert-butylnitrone

α-(3,5-dimethoxy-4-hydroxyphenyl)-N-tert-butylnitrone

α-(3,5-di-tert-butyl-4-hydroxyphenyl)-N-tert-butylnitrone

α-(2-hydroxyphenyl)-N-tert-butylnitrone, and

α-(2,4,6-trihydroxyphenyl)-N-tert-butylnitrone.

10. The ophthalmic pharmaceutical composition of claim 9 wherein the compound is α-(phenyl)-N-tert-butylnitrone.

11. The ophthalmic pharmaceutical composition of claim 9 wherein the compound is α-(3,5-dimethoxy-4-hydroxyphenyl)-N-tert-butylnitrone.

12. A method for treating a mammal with ocular inflammation which method comprises administering to said mammal a pharmaceutical composition comprising a pharmaceutically acceptable inert carrier and an ocular inflammation-treating amount of a compound of formula I:

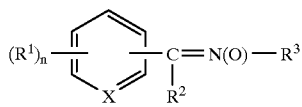

I wherein
each $R^1$ is independently selected from the group consisting of alkyl, lower alkoxy, aminoacyl, acyloxy, hydroxy and —$CO_2Y$, wherein Y is hydrogen or a pharmaceutically acceptable salt;

$R^2$ is selected from the group consisting of hydrogen, alkyl and aryl;

$R^3$ is selected from the group consisting of alkyl, alkenyl, alkynyl, aryl, alkaryl, alkcycloalkyl, cycloalkyl and cycloalkenyl;

X is CH; and n is an integer from 0 to 3.

13. The method of claim 12 wherein said pharmaceutical composition is administered topically.

14. The method of claim 13 wherein said pharmaceutical composition is administered as eye drops.

15. The method of claim 13 wherein said pharmaceutical composition is administered as an ophthalmic salve or ointment.

16. The method of claim 12 wherein said pharmaceutical composition is administered systemically.

17. The method of claim 16 wherein said pharmaceutical composition is administered orally.

18. The method of claim 16 wherein said pharmaceutical composition is administered parenterally.

19. The method of claim 18 wherein said pharmaceutical composition is administered by injection.

20. The method of claim 12 wherein said compound is selected from the group consisting of:

α-(phenyl)-N-tert-butylnitrone

α-(3,5-dimethoxy-4-hydroxyphenyl)-N-tert-butylnitrone

α-(3,5-di-tert-butyl-4-hydroxyphenyl)-N-tert-butylnitrone

α-(2-hydroxyphenyl)-N-tert-butylnitrone, and

α-(2,4,6-trihydroxyphenyl)-N-tert-butylnitrone.

21. The method of claim 20 wherein the compound is α-(phenyl)-N-tert-butylnitrone.

22. The method of claim 20 wherein the compound is α-(3,5-dimethoxy-4-hydroxyphenyl)-N-tert-butylnitrone.

23. A compound selected from the group consisting of:

α-(3,5-dimethoxy-4-hydroxyphenyl)-N-tert-butylnitrone, and

α-(2,4,6-trihydroxyphenyl)-N-tert-butylnitrone.

24. α-(3,5-Dimethoxy-4-hydroxyphenyl)-N-tert-butylnitrone.

25. α-(2,4,6-Trihydroxyphenyl)-N-tert-butylnitrone.

26. A pharmaceutical composition comprising a pharmaceutically acceptable inert carrier and an inflammation-treating amount of a compound selected from the group consisting of:

α-(3,5-dimethoxy-4-hydroxyphenyl)-N-tert-butylnitrone, and

α-(2,4,6-trihydroxyphenyl)-N-tert-butylnitrone.

27. A method for treating a mammal with inflammation which method comprises administering to said mammal a pharmaceutical composition comprising a pharmaceutically acceptable inert carrier and an inflammation-treating amount of a compound selected from the group consisting of:

α-(3,5-dimethoxy-4-hydroxyphenyl)-N-tert-butylnitrone, and

α-(2,4,6-trihydroxyphenyl)-N-tert-butylnitrone.

28. An ophthalmic pharmaceutical composition comprising a pharmaceutically acceptable ophthalmic carrier and an ocular inflammation-treating amount of 5,5-dimethylpyrroline-N-oxide.

29. A method for treating a mammal with ocular inflammation which method comprises administering to said mammal a pharmaceutical composition comprising a pharmaceutically acceptable inert carrier and an ocular inflammation-treating amount of 5,5-dimethylpyrroline-N-oxide.

* * * * *